United States Patent
Klase

(10) Patent No.: US 11,554,123 B2
(45) Date of Patent: Jan. 17, 2023

(54) COMPOSITIONS AND METHODS FOR REACTIVATING LATENT HIV-1 INFECTIONS

(71) Applicant: Saint Joseph's University, Philadelphia, PA (US)

(72) Inventor: Zachary A. Klase, Sewell, NJ (US)

(73) Assignee: Saint Joseph's University, Philadelphia, PA (US)

( * ) Notice: Subject to any disclaimer, the term of this patent is extended or adjusted under 35 U.S.C. 154(b) by 0 days.

(21) Appl. No.: 16/489,658

(22) PCT Filed: Feb. 28, 2018

(86) PCT No.: PCT/US2018/020192
§ 371 (c)(1),
(2) Date: Aug. 28, 2019

(87) PCT Pub. No.: WO2018/160676
PCT Pub. Date: Sep. 7, 2018

(65) Prior Publication Data
US 2020/0016168 A1 Jan. 16, 2020

Related U.S. Application Data

(60) Provisional application No. 62/465,580, filed on Mar. 1, 2017.

(51) Int. Cl.
*A61K 31/5513* (2006.01)
*A61P 31/18* (2006.01)
*A61K 31/165* (2006.01)
*A61K 31/167* (2006.01)
*A61K 31/404* (2006.01)

(52) U.S. Cl.
CPC ........ *A61K 31/5513* (2013.01); *A61K 31/165* (2013.01); *A61K 31/167* (2013.01); *A61K 31/404* (2013.01); *A61P 31/18* (2018.01)

(58) Field of Classification Search
None
See application file for complete search history.

(56) References Cited

U.S. PATENT DOCUMENTS 6,653,081 B2 * 11/2003 Whitcomb ............. C12Q 1/703
424/188.1
8,883,851 B2 * 11/2014 Gore ..................... C07C 259/06
514/575

2004/0006072 A1 1/2004 Franz et al.
2009/0258865 A1 * 10/2009 Cartt ..................... A61K 31/355
514/221
2011/0281950 A1 11/2011 Baiocchi
2014/0199260 A1 7/2014 Finkel et al.
2016/0095850 A1 4/2016 Cooper et al.

FOREIGN PATENT DOCUMENTS

WO 2011097166 A2 8/2011
WO 2013148197 A1 10/2013

OTHER PUBLICATIONS

Filippakopoulos, et al., "Benzodiazepines and benzotriazepines as protein interaction inhibitors targeting bromodomains of the BET family", Bioorganic & Medicinal Chemistry, vol. 20, Issue 6, Mar. 15, 2012, pp. 1878-1886.
Klase, et al., "Activation of HIV-1 from Latent Infection via Synergy of RUNX1 Inhibitor Ro5-3335 and SAHA", PLOS Pathogens, vol. 10, Issue 3, Mar. 20, 2014, pp. 1-12.
PCT International Search Report & Written Opinion dated May 15, 2018 for International Application No. PCT/US2018/020192.
"Xanax(R) alprazolam tablets, USP, C-IV", Pharmacia & Upjohn Co., Division of Pfizer, Inc., Medication Guide, Rev. Sep. 2016, 26 pgs.
Alamer, et al., "Modulation of BRD4 in HIV epigenetic regulation: implications for finding an HIV cure", Retrovirology, 18(3), 2021, 9 pages.
Conrad, et al., "The Short Isoform of BRD4 Promotes HIV-1 Latency by Engaging Repressive SWI/SNF Chromatin Remodeling Complexes", Mol Cell, 67(6), 2017, pp. 1001-1012.
Huang, et al., "A Novel Bromodomain Inhibitor Reverses HIV-1 Latency through Specific Binding with BRD4 to Promote Tat and P-TEFb Association", Front Microbiol, 8(1035), 2017, 11 pages.

* cited by examiner

Primary Examiner — Savitha M Rao
Assistant Examiner — Gregg Polansky
(74) Attorney, Agent, or Firm — Saul Ewing LLP; Domingos J. Silva; Chihao Wang

(57) ABSTRACT

The present invention relates in part to the discovery that benzodiazepines can be used to reactivate latent HIV-1 virus that is integrated into human genome. In other embodiments, the benzodiazepine is used in combination with a histone deacetylase inhibitor (HDACi), such as but not limited to SAHA (also known as N-hydroxy-N-phenyl-octanediamide, Suberoylanilide hydroxamic acid, Vorinostat). In yet other embodiments, the combination of benzodiazepine and the HDACi synergistically reactivates latent HIV-1 virus that is integrated into human genome, with minimal or no significant toxicity associated with the dose of either agent.

10 Claims, 12 Drawing Sheets

Specification includes a Sequence Listing.

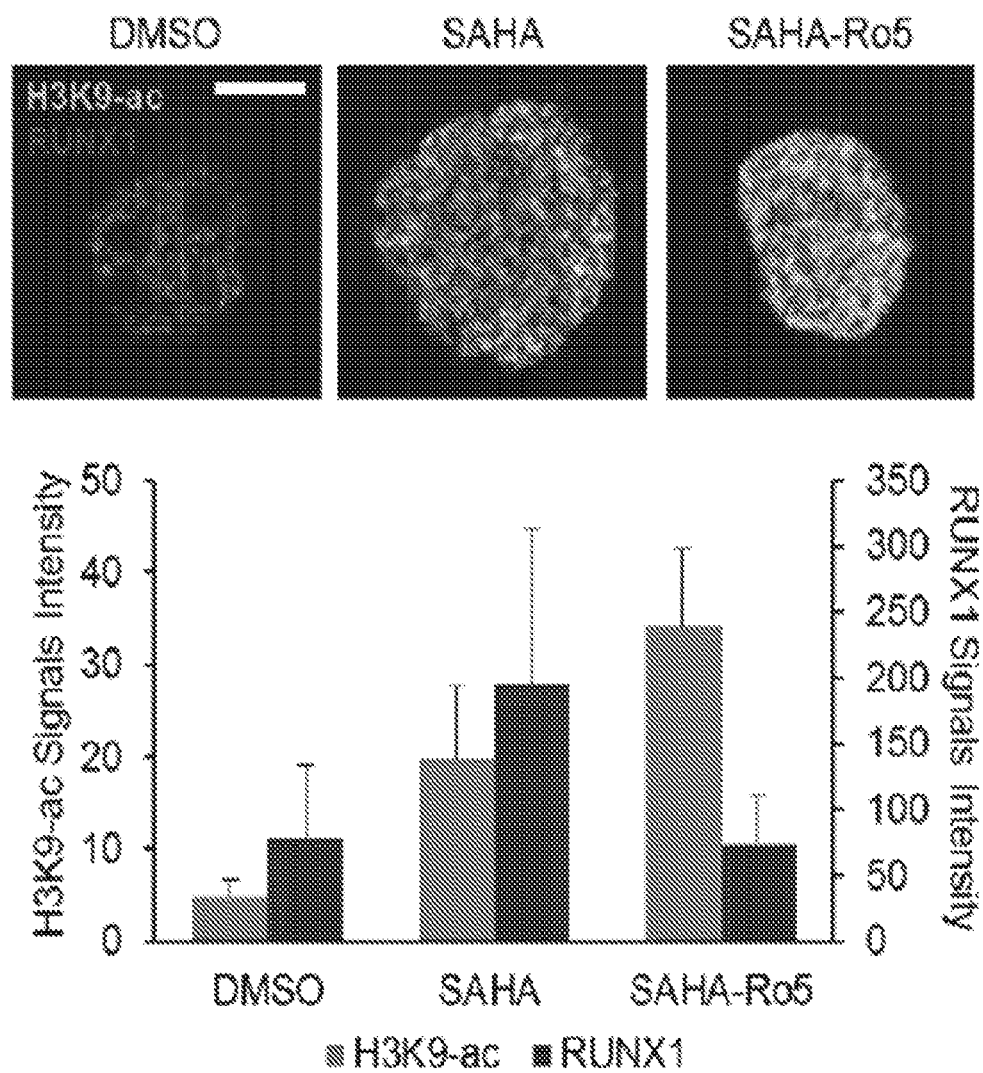

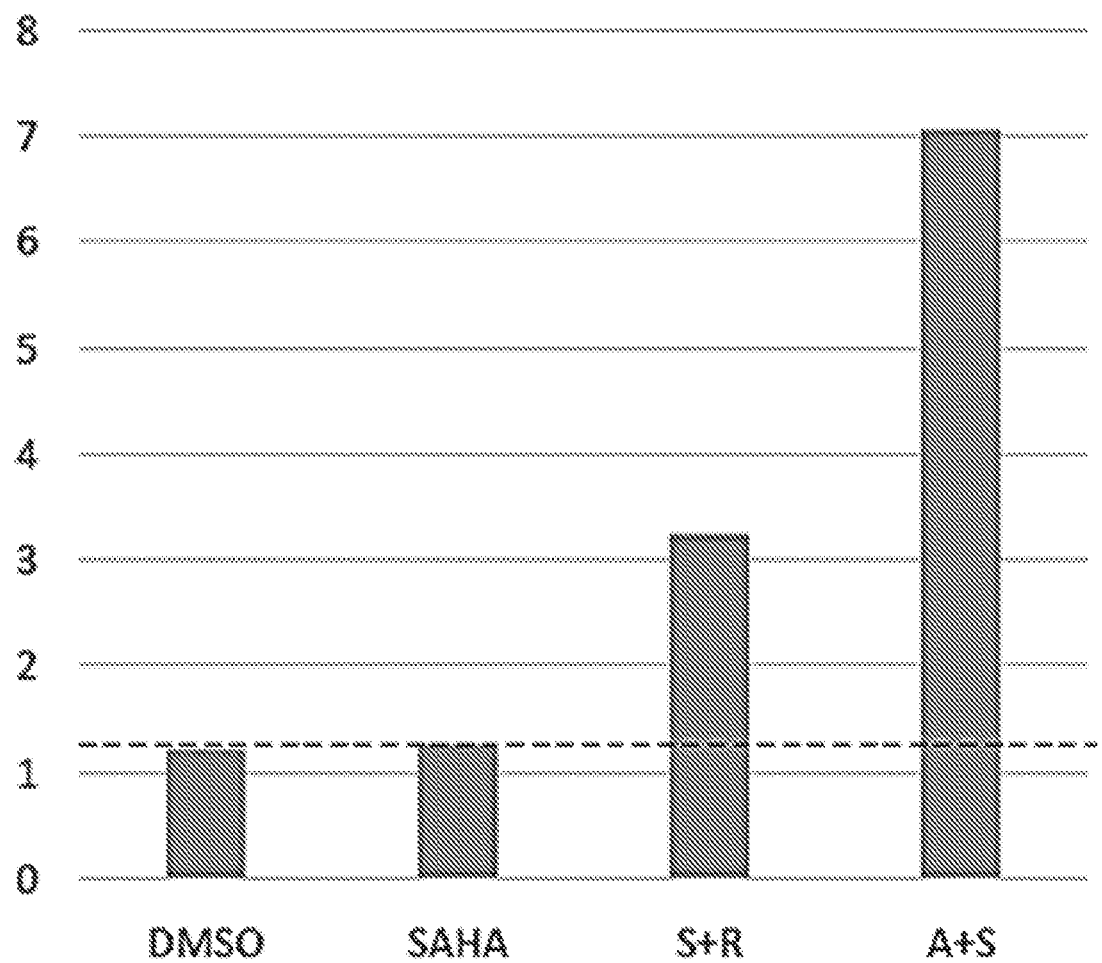

COMPOSITIONS AND METHODS FOR REACTIVATING LATENT HIV-1 INFECTIONS

CROSS-REFERENCE TO RELATED APPLICATIONS

The present application is a 35 U.S.C. § 371 national phase application of, and claims priority to, International Application No. PCT/US2018/020192, filed Feb. 28, 2018, which claims priority under 35 U.S.C. § 119(e) to U.S. Provisional Patent Application No. 62/465,580, filed Mar. 1, 2017, all of which applications are hereby incorporated by reference in their entireties herein.

STATEMENT REGARDING FEDERALLY SPONSORED RESEARCH OR DEVELOPMENT

This invention was made with government support under grant number 1DP2DA044550-01 awarded by the National Institute on Drug Abuse (National Institutes of Health). The government has certain rights in the invention.

BACKGROUND OF THE INVENTION

The major challenge for human immunodeficiency virus type 1 (HIV-1) treatment is the viral reservoir harbored by resting memory CD4+ T cells, which is established early during infection. These cells have a very long half-life and resist apoptosis. In these cells, integrated proviral genome undergoes transcriptional silencing and persists for many years, cannot be detected by the immune system, and are not reached by traditional therapies. Once HIV-1 patients quit highly active antiretroviral therapy (HAART), the virus can be activated in a patient's body.

Recent studies propose a way to eradicate HIV-1 through activation of the silenced virus in resting memory CD4+ cells through a "shock and kill" approach. In this approach, HIV-1 virus would be activated using latency reversing agents (LRAs), and infected cells would then be depleted by viral cytopathic effect, host immune response, and/or a second intervention. At the same time, new infection to other cells would be controlled using HAART. Various LRAs have been proposed, but thus far they have failed to eradicate the HIV-1 reservoir in the clinical trials. These LRAs work through interfering with cellular mechanisms that are involved in maintaining HIV-1. The current commonly targeted mechanisms that researchers investigate to purge HIV-1 viral reservoir include (i) histone deacetylase (HDAC) inhibitors such as panopinostat, suberoylanilide hydroxamic acid (SAHA; Vorinostat) and Trichostatin-A; (ii) bromodomain-containing proteins inhibitors such as JQ1, and (iii) PKC agonists, which work through activation of NF-kβ such as prostratin, bryostatin and ingenol. Some HDAC inhibitors, such as SAHA, are FDA approved and have been used as anticancer therapeutic agents. However, SAHA and all other suggested treatments are unsuccessful in decreasing the size of the latent HIV-1 pool. Therefore, there is a need to find other therapeutic agents that can synergize with SAHA to enhance its efficiency and minimize its side effects.

An important transcription factor necessary for T cell development and differentiation is Runt-related transcription factor1 (RUNX1), also known as acute myeloid leukemia 1 protein (AML1) or core-binding factor subunit alpha-2 (CBFA2). It is one of three RUNX family proteins that possess a highly conserved 128 amino acid Runt DNA-binding domain at the N-terminus. The Runt domain is important for binding with consensus sequence (PyGPyGGTPy) in DNA and with core binding factor subunit beta (CBF-β). CBF-β heterodimerizes with RUNX1 and enhances RUNX1 affinity to the DNA 10 fold and stabilizes RUNX proteins against proteolytic degradation. RUNX proteins contain a nuclear localization signal that allows the transport of the CBFβ-RUNX complex to the nucleus and regulates gene expression. The RUNX proteins are highly similar and share a common DNA binding site. However, they share different physiologic functions. RUNX1 and CBFβ knockout in mice is embryonic lethal. RUNX1 plays an essential role in hematopoiesis and the development of cell types such as lymphoid cells, erythroid cells, granulocytes, and macrophages. Moreover, RUNX1 is necessary for the development of CD8+ T cells. RUNX1 is downregulated during the development of thymocytes from double negative (CD4− and CD8−) to double positive (CD4+ and CD8+) lymphocytes. RUNX1 is also downregulated when naïve CD4+ T cells are stimulated through T cell receptor (TCR) to become effector CD4+ T cells. Downregulation of RUNX1 contributes to the production of IL-2.

According to its posttranslational modifications and the context in which it is recruited, RUNX1 functions to activate or repress gene transcription. It can initiate transcription through recruitment of p300 histone acetyltransferase. On the other hand, it may repress transcription through recruitment of repressive factors such as mSin3A, Suv39H1, and histone deacetylases. Furthermore, RUNX1 physically interacts with the STATS transcription factor and this interaction serves to regulate either RUNX1 or STATS function. The U3 region of HIV-1 contains a potential binding site for RUNX1 protein. Interestingly, overexpression of RUNX1 and/or CBF-β inhibits HIV-1 transcription. Moreover, inhibition of RUNX1 or CBF-β with siRNA significantly increases HIV-1 transcription. Furthermore, the benzodiazepine, Ro5-3335, an inhibitor of RUNX-1/CBFβ function, synergizes with SAHA, an HDAC3 inhibitor, in activating HIV-1 transcription. Ro5-3335 is a benzodiazepine with demonstrated potency and safety in treating acute myeloid leukemia (AML) in a mouse model.

There remains a need in the art for compositions and methods for treating HIV-1 infection. In certain embodiments, such compositions and methods should treat HIV-1 by reactivating latent HIV-1 lying dormant in CD4+ T cells. The present invention addresses these needs.

BRIEF SUMMARY OF THE INVENTION

In certain embodiments, the invention provides a composition comprising at least one benzodiazepine or a salt or solvate thereof, and at least one histone deacetylase inhibitor or a salt or solvate thereof, wherein the benzodiazepine is not Ro5-3335. In other embodiments, the benzodiazepine is at least one selected from the group consisting of Alprazolam, Bromazepam, Clobazam, Clonazepam, Clorazepate, Diazepam, Estazolam, and Flunitrazepam. In yet other embodiments, the at least one histone deacetylase inhibitor is selected from the group consisting of vorinostat (also known as N-hydroxy-N'-phenyloctanediamide or SAHA), belinostat (also known as (2E)-N-Hydroxy-3-[3-(phenylsulfamoyl)phenyl]prop-2-enamide), LAQ824 (also known as (E)-3-(4-(((2-(1H-indol-3-yl)ethyl)(2-hydroxyethy)amino)methyl)phenyl)-N-hydroxyacrylamide), panobinostat (also known as (2E)-N-hydroxy-3-[4-({[2-(2-methyl-1H-indol-3-yl)ethyl]amino}methyl) phenyl]acrylamide), givinostat (also known as {6-[(diethylamino)methyl]naphthalen-2- yl}methyl [4-(hydroxycarbamoyl)phenyl]carbamate), pyroxamide (also known as N1-Hydroxy-N8-3-pyridinyl-octanediamide), trichostatin A (also known as [R-(E,E)]-7-[4-(Dimethylamino)phenyl]-N-hydroxy-4,6-dimethyl-7-oxo-2,4-heptadienamide), CBHA (m-carboxycinnamic acid bis-hydroxamide), and any combinations thereof.

In certain embodiments, the composition comprises about 0.5 mg to about 10 mg benzodiazepine. In other embodiments, the composition comprises about 40 mg to about 400 mg histone deacetylase inhibitor.

In certain embodiments, the composition is a pharmaceutically acceptable composition further comprising at least one pharmaceutically acceptable excipient. In other embodiments, the composition further comprises at least one additional compound useful for preventing and/or treating HIV, which is selected from the group consisting of antiretroviral drugs, nucleoside/nucleotide reverse transcriptase inhibitors (NRTIs), non-nucleoside reverse transcriptase inhibitors (NNRTIs), protease inhibitors (PIs), fusion inhibitors, CCR5 antagonists, and integrase inhibitors.

The invention further provides a kit comprising a composition of the invention and instructional material comprising instructions for treating HIV-1 infection in a subject in need thereof using the composition.

In other aspects, the invention provides a method of treating or preventing HIV infection in a subject in need thereof, the method comprising administering to the subject a therapeutically effective amount of a benzodiazepine or a salt or solvate thereof, wherein the benzodiazepine is not Ro5-3335. In certain embodiments, the administration of the benzodiazepine reactivates latent HIV-1 virus that has been integrated into the genome of the subject. In other embodiments, the benzodiazepine is at least one selected from the group consisting of Alprazolam, Bromazepam, Clobazam, Clonazepam, Clorazepate, Diazepam, Estazolam, and Flunitrazepam. In yet other embodiments, the therapeutically effective amount of the benzodiazepine is an amount sufficient to yield a benzodiazepine blood serum concentration in the subject of about 10 nM to about 10 µM.

In certain embodiments, the method further comprises administering to the subject a therapeutically effective amount of a histone deacetylase inhibitor. In other embodiments, the histone deacetylase inhibitor is selected from the group consisting of vorinostat, LAQ824, panobinostat, givinostat, pyroxamide, trichostatin A, CBHA, and any combinations thereof. In yet other embodiments, the therapeutically effective amount of the histone deacetylase inhibitor is an amount sufficient to yield a histone deacetylase inhibitor blood serum concentration in the subject of about 10 nM to about 10 µM.

In certain embodiments, the benzodiazepine and the histone deacetylase inhibitor act synergistically to reactivate latent HIV-1 virus in the subject.

In certain embodiments, the method further comprises administering to the subject at least one additional compound useful for preventing and/or treating HIV, which is selected from the group consisting of antiretroviral drugs, nucleoside/nucleotide reverse transcriptase inhibitors (NRTIs), non-nucleoside reverse transcriptase inhibitors (NNRTIs), protease inhibitors (PIs), fusion inhibitors, CCR5 antagonists, and integrase inhibitors.

BRIEF DESCRIPTION OF THE FIGURES

For the purpose of illustrating the invention, depicted in the drawings are certain embodiments of the invention. However, the invention is not limited to the precise arrangements and instrumentalities of the embodiments depicted in the drawings.

FIG. 3A is a set of fluorescent images and a graph showing treatment of cells with SAHA and SAHA+Ro5-3335 led to an increase in acetylated histone 3 at lysine 9 (H3K9) in the nuclei of the cells. Fluorescent imaging also showed that Ro5-3335 inhibited RUNX1 function as indicated by a decrease in RUNX1 detection.

FIGS. 3B-3D are a set of graphs showing the results of chromatin immunoprecipitation (ChIP) assays to determine the presence of proteins and modifications at the integrated HIV-1 long terminal repeat (LTR) in TZMb1 cells, after exposure to SAHA (S), Ro5-3335 (R), Alprazolam (A) and Clonazepam (C). FIG. 3B shows acetylation of H3K9, FIG. 3C shows recruitment of STATS, and FIG. 3D shows recruitment of CBP/P300.

DETAILED DESCRIPTION OF THE INVENTION

Figure 1A:
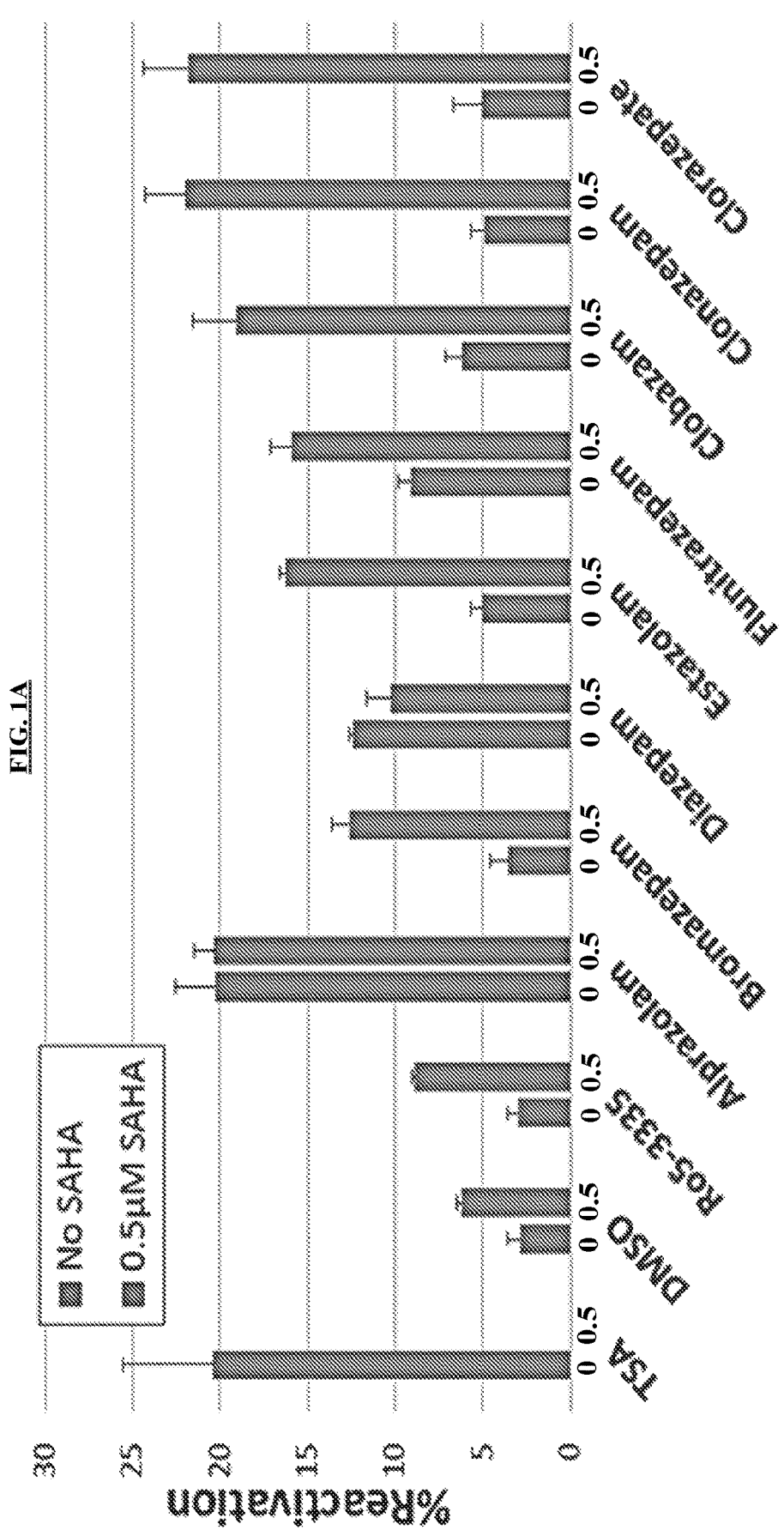
FIGS. 1A-1B are graphs reporting reactivation of latent HIV-1 in a JLat10.6 cell line model of T-cell latency by administration of benzodiazepine drugs alone or in combination with suberoylanilide hydroxamic acid (SAHA).

The present invention relates to the discovery that benzodiazepines reactivate latent HIV-1, both when administered alone and when administered in combination with a histone deacetylase inhibitor. In certain embodiments, the benzodiazepine is at least one selected from the group consisting of Alprazolam, Bromazepam, Clobazam, Clonazepam, Clorazepate, Diazepam, Estazolam, and Flunitrazepam. In other embodiments, the histone deacetylase inhibitor is N-hydroxy-N'-phenyl-octanediamide (suberoylanilide hydroxamic acid; SAHA; Vorinostat).

Compositions

In one aspect, the invention provides a composition comprising at least one benzodiazepine and at least one histone deacetylase inhibitor.

In certain embodiments, the benzodiazepine is at least one selected from the group consisting of Alprazolam, Bromazepam, Clobazam, Clonazepam, Clorazepate, Diazepam, Estazolam, and Flunitrazepam. In other embodiments, the benzodiazepine is not Ro5-3335. In other embodiments, the benzodiazepine is Ro5-3335.

In certain embodiments, the at least one histone deacetylase inhibitor is selected from the group consisting of vorinostat (also known as N-hydroxy-N'-phenyloctanediamide or SAHA), belinostat (also known as (2E)-N-Hydroxy-3-[3-(phenylsulfamoyl)phenyl]prop-2-enamide), LAQ824 (also known as (E)-3-(4-(((2-(1H-indol-3-yl)ethyl)(2-hydroxyethyl) amino)methyl)phenyl)-N-hydroxyacrylamide), panobinostat (also known as (2E)-N-hydroxy-3-[4-({[2-(2-methyl-1H-indol-3-yl)ethyl]amino}methyl)phenyl] acrylamide), givinostat (also known as {6-[(diethylamino) methyl]naphthalen-2-yl}methyl [4-(hydroxycarbamoyl) phenyl]carbamate), pyroxamide (also known as N1-Hydroxy-N8-3-pyridinyl-octanediamide), trichostatin A (also known as [R-(E,E)]-7-[4-(Dimethylamino)phenyl]-N-hydroxy-4,6-dimethyl-7-oxo-2,4-heptadienamide), CBHA (m-carboxycinnamic acid bis-hydroxamide), and any combinations thereof.

In certain embodiments, the composition is formulated as a pharmaceutically acceptable composition. In other embodiments, the pharmaceutically acceptable composition further comprises at least one pharmaceutically acceptable excipient. In other embodiments, the pharmaceutically acceptable composition consists of at least one pharmaceutically acceptable excipient, at least one benzodiazepine, and at least one histone deacetylase inhibitor.

In certain embodiments, the composition comprises about 10 nM to about 10 µM benzodiazepine. In other embodiments, the composition comprises about 0.5 mg to about 10 mg benzodiazepine.

In certain embodiments, the composition comprises about 10 nM to about 1 µM histone deacetylase inhibitor. In other embodiments, the composition comprises about 40 mg to about 400 mg histone deacetylase inhibitor.

In certain embodiments, the composition comprises N-hydroxy-N'-phenyl-octanediamide, and at least one selected from the group consisting of Alprazolam, Clobazam, and Clonazepam.

In certain embodiments, the composition further comprises at least one additional compound useful for preventing and/or treating HIV. Non-limiting examples of compounds and agents useful for preventing and/or treating HIV include, but are not limited to, antiretroviral drugs, nucleoside/nucleotide reverse transcriptase inhibitors (NRTIs), non-nucleoside reverse transcriptase inhibitors (NNRTIs), protease inhibitors (PIs), fusion inhibitors, CCR5 antagonists, and integrase inhibitors.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereoisomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}F$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

The invention further includes a pharmaceutical composition comprising the compound of the invention and a pharmaceutically acceptable carrier. In certain embodiments, the pharmaceutical composition further comprises at least one additional agent that is useful to treat the diseases or disorders contemplated herein. In certain embodiments, the compound of the invention and the additional agent are coformulated in the composition.

Salts

The compounds described herein may form salts with acids or bases, and such salts are included in the present invention. In certain embodiments, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts can be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids can be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts can be prepared from the corresponding compound by reacting, for example, the appropriate acid or base with the compound.

Methods

In another aspect, the invention further provides a method of treating HIV infection in a subject in need thereof. In certain embodiments, the method comprises administering to the subject a therapeutically effective amount of a benzodiazepine. In certain embodiments, the administration of the benzodiazepine reactivates latent HIV-1 virus that has been integrated into the genome of the subject.

In certain embodiments, the benzodiazepine is at least one selected from the group consisting of Alprazolam, Bromazepam, Clobazam, Clonazepam, Clorazepate, Diazepam, Estazolam, and Flunitrazepam. In other embodiments, the benzodiazepine is not Ro5-3335.

In certain embodiments, the method further comprises administering to the subject a therapeutically effective amount of a histone deacetylase inhibitor. In other embodiments, the histone deacetylase inhibitor is selected from the group consisting of vorinostat, belinostat, LAQ824, panobinostat, givinostat, pyroxamide, trichostatin A, CBHA, and any combinations thereof.

In certain embodiments, the method comprises administering to the subject a therapeutically effective amount of a composition of the invention.

In certain embodiments, the therapeutically effective amount of the benzodiazepine is an amount sufficient to yield a blood serum concentration in the subject of about 10 nM to about 10 μM.

In certain embodiments, the therapeutically effective amount of the histone deacetylase inhibitor is an amount sufficient to yield a blood serum concentration in the subject of about 10 nM to about 10 μM.

In certain embodiments, the benzodiazepine and the histone deacetylase inhibitor act synergistically to reactivate latent HIV-1 virus in the subject, such that the combined effect of the two drugs is greater than the additive effect of each drug alone. In certain embodiments, the synergistic effect allows for a smaller therapeutically effective dose to be administered than if either drug was administered alone, thereby reducing the severity of any harmful side effects from either of these two drugs.

In certain embodiments, the subject does not experience significant toxicity or harmful side effects from the administration of the benzodiazepine and/or the histone deacetylase inhibitor.

Kits

The invention includes a kit comprising a composition of the invention and an instructional material for use thereof. The instructional material included in the kit comprises instructions for preventing or treating a disorder or disease contemplated within the invention in a subject. The instructional material recites the amount of, and frequency with which, the compound(s) of the invention should be administered to the subject. In certain embodiments, the kit further comprises at least one additional agent useful to treat or prevent a disease or disorder contemplated within the invention.

Combination and Concurrent Therapies

In certain embodiments, the compositions of the invention are useful in the methods of present invention when used concurrently with at least one additional compound useful for preventing and/or treating diseases and/or disorders contemplated herein.

In certain embodiments, the compositions of the invention are useful in the methods of present invention in combination with at least one additional compound useful for preventing and/or treating HIV infection.

Non-limiting examples of compounds and agents useful for preventing and/or treating HIV include, but are not limited to, antiretroviral drugs, nucleoside/nucleotide reverse transcriptase inhibitors (NRTIs), non-nucleoside reverse transcriptase inhibitors (NNRTIs), protease inhibitors (PIs), fusion inhibitors, CCR5 antagonists, and integrase inhibitors.

These additional compounds may comprise compounds of the present invention or other compounds, such as commercially available compounds, known to treat, prevent, or reduce the symptoms of diseases and/or disorders contemplated herein. In certain embodiments, the combination of at least one compound of the invention or a salt thereof, and at least one additional compound useful for preventing and/or treating diseases and/or disorders contemplated herein, has additive, complementary or synergistic effects in the prevention and/or treatment of diseases and/or disorders contemplated herein.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

In certain embodiments, the compound and the agent are physically mixed in the composition. In other embodiments, the compound and the agent are physically separated in the composition.

A synergistic effect can be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations can be administered to the subject either prior to or after the onset of a disease or disorder contemplated in the invention. Further, several divided dosages, as well as staggered dosages can be administered daily or sequentially, or the dose can be continuously infused, or can be a bolus injection. Further, the dosages of the therapeutic formulations can be proportionally increased or decreased as indicated by the exigencies of the therapeutic or prophylactic situation.

Administration of the compositions of the present invention to a patient, preferably a mammal, more preferably a human, can be carried out using known procedures, at dosages and for periods of time effective to treat a disease or disorder contemplated in the invention. An effective amount of the therapeutic compound necessary to achieve a therapeutic effect can vary according to factors such as the state of the disease or disorder in the patient; the age, sex, and weight of the patient; and the ability of the therapeutic compound to treat a disease or disorder contemplated in the invention. Dosage regimens can be adjusted to provide the optimum therapeutic response. For example, several divided doses can be administered daily or the dose can be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention can be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In certain embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier can be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration can be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-Alzheimer's Disease agents, anti-tuberculosis agents.

Routes of administration of any of the compositions of the invention include oral, nasal, rectal, intravaginal, parenteral, buccal, sublingual or topical. The compounds for use in the invention can be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use can be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets can be uncoated or they can be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time can be as long as a month or more and should be a release which is longer that the same amount of agent administered in bolus form.

For sustained release, the compounds can be formulated with a suitable polymer or hydrophobic material that provides sustained release properties to the compounds. As such, the compounds for use the method of the invention can be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention can be in the range of from about 0.01 mg to about 5,000 mg per day, such as from about 0.1 mg to about 1,000 mg, for example, from about 1 mg to about 500 mg, such as about 5 mg to about 250 mg per day. The dose can be administered in a single dosage or in multiple dosages, for example from 1 to 4 or more times per day. When multiple dosages are used, the amount of each dosage can be the same or different. For example, a dose of 1 mg per day can be administered as two 0.5 mg doses, with about a 12-hour interval between doses.

It is understood that the amount of compound dosed per day can be administered, in non-limiting examples, every day, every other day, every 2 days, every 3 days, every 4 days, or every 5 days. For example, with every other day administration, a 5 mg per day dose can be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "patient," "subject," "individual" and the like are used interchangeably, and refer to any animal, or cells thereof whether in vitro or in situ, amenable to the methods described herein. In a non-limiting embodiment, the patient, subject or individual is a human.

As used herein, the term "therapeutic" treatment refers to a treatment administered to a subject who exhibits signs of pathology, for the purpose of diminishing or eliminating those signs.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments can be specifically tailored or modified, based on knowledge obtained from the field of pharmacogenomics.

The term "prevent", "preventing" or "prevention", as used herein, means avoiding or delaying the onset of symptoms associated with a disease or condition in a subject that has not developed such symptoms at the time the administering of an agent or compound commences.

As used herein, the terms "effective amount", "pharmaceutically effective amount" and "therapeutically effective amount" refer to a nontoxic but sufficient amount of an agent to provide the desired biological result. That result can be reduction and/or alleviation of the signs, symptoms, or causes of a disease, or any other desired alteration of a biological system. An appropriate therapeutic amount in any individual case can be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

In one aspect, the terms "co-administered" and "co-administration" as relating to a subject refer to administering to the subject a compound of the invention or salt thereof along with a compound that may also treat the disorders or diseases contemplated within the invention. In certain embodiments, the co-administered compounds are administered separately, or in any kind of combination as part of a single therapeutic approach. The co-administered compound can be formulated in any kind of combinations as mixtures of solids and liquids under a variety of solid, gel, and liquid formulations, and as a solution.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "effective amount" or "therapeutically effective amount" of a compound is that amount of compound that is sufficient to provide a beneficial effect to the subject to which the compound is administered.

As used herein, an "instructional material" includes a publication, a recording, a diagram, or any other medium of expression that can be used to communicate the usefulness of a composition or method of the invention in the kit for treating, preventing or alleviating various diseases or disorders recited herein. Optionally, or alternately, the instructional material can describe one or more methods of treating, preventing or alleviating diseases or disorders in a cell or a tissue of a mammal. The instructional material of the kit of the invention can, for example, be affixed to a container that contains the identified composition or delivery system of the invention or be shipped together with a container that contains the identified composition or delivery system. Alternatively, the instructional material can be shipped separately from the container with the intention that the instructional material and the composition be used cooperatively by the recipient.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 and the like, as well as individual numbers within that range, for example, 1, 2, 2.7, 3, 4, 5, 5.3, and 6. This applies regardless of the breadth of the range.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

JLat10.6 Reactivation Protocol

JLat10.6 cells were cultured in the presence of increasing concentrations of the indicated benzodiazepines in the presence or absence of 1 µM SAHA. Forty-eight hours after treatment, cells were stained for live dead staining using Live/Dead Red stain (BD Biosciences). The percentage of GFP positive cells was determined by flow cytometry on a CYTEK® DxP12 flow cytometer.

JLat10.6 Cell Viability Protocol

JLat10.6 cells were cultured in the presence of increasing concentrations of the indicated benzodiazepines in the presence or absence of 1 µM SAHA. Forty-eight hours after treatment, cells were stained for live dead staining using Live/Dead Red stain (BD Biosciences). Viability was determined by fluorescent detection of the live dead stain using a CYTEK® DxP12 flow cytometer. Comparison to untreated cells was used to determine degree of cell viability.

T Cell Activation Protocol

To investigate whether alprazolam is specifically activating HIV-1 or having general effect on T cell activation (CD4 and CD8), primary PBMC from two healthy donors were treated with 10 µM, 50 µM Alprazolam or Ro5-3335 respectively alone or in combination with 0.5 µM SAHA. Twenty-four hours after treatment, cells were stained using Zombie yellow live and dead staining and then stained for CD3, CD8, CD4, CD69, and then fixed for analysis by flow cytometry. AntiCD3/CD28 and PHA were included as a positive control. Samples were analyzed on a CYTEK® DxP12 flow cytometer followed by analysis using FLOWJO® v10 software (Treestar)

NUCLEO-M Protocol

Transcriptionally competent nuclei were isolated from TZM-bl cells by chemical lysis and stored following manufacturer's recommendations (Nuclei Isolation Kit: Nuclei EZ Prep, Sigma-Aldrich, Nuc-101). Nuclei were stained for 1 hour on ice in 5% FBS/PBS solution containing primary antibodies. Nuclei were washed twice in 5% FBS/PBS and stained for 1 hour on ice with appropriate secondary antibodies conjugated with fluorescent dyes. Nuclei were finally washed twice in 5% FBS/PBS and resuspended in the storage buffer provided by the kit (Nuclei Isolation Kit: Nuclei EZ Prep, Sigma-Aldrich, Nuc-101).

Isolated nuclei and TZM-bl cells seeded on a chambered coverglass (NUNC® LAB-TEK® Chambered Coverglass, Thermo Fisher) were imaged with a Zeiss AXIOVERT® microscope with a Zeiss alpha PLAN-FLUAR® 100×, 1.45 N.A., oil objective and a spinning disk confocal scan head (Yokogawa CSU-X1). A 488 nm laser source with 488-25 nm, 617-73 nm and 692-40 nm emission filters were used for the illumination of Alexa Fluor® 488 dye (Thermo Fisher) or SYTO® RNA SELECT® Green Fluorescent cell Stain (Thermo Fisher), and PerCP-Cy5.5 (BD Biosciences) respectively. A 561 nm laser source with 568-25 nm emission filters was used for illumination of ALEXA FLUOR® 555 dye (Thermo Fisher). Digital images were captured sequentially by a high-speed EM-CCD camera with 100 ms exposure time (Photometrics EVOLVE® 512). Confocal z-stacks of the entire nucleus or of the nuclear equator were acquired with a z-step size of 0.4-1 µm. Time-lapse experiments were automated by software (SLIDEBOOK® 6.0.9, 3i).

Chromatin Immunoprecipitation Protocols

TZMbl cells were cultured with benzodiazepines for 48 hours before chromatin immunoprecipitation analysis. Following treatment, cells were processed for chromatin immunoprecipitation using the Pierce Agarose ChIP Kit (Fisher Scientific) using commercially available antibodies against histone H3 lysine 9 acetylation, STAT5, and CBP/P300. Degree of occupancy at the integrated HIV-1 LTR was determined by qPCR using HIV-1 LTR specific primers run on a BioRad CFX384 qPCR machine using Sybr Green methodology.

Luciferase Assay Protocols

For determination of HIV-1 LTR reactivation in TZMbl cells, cultures were treated with benzodiazepines or SAHA for 48 hours. Following treatment, cell lysates were prepared using GLOLYSIS® buffer (PROMEGA®) and luciferase activity was determined using BRIGHTGLO® Luciferase Reagent (PROMEGA®) and read on a spectrophotometer following manufacturer's instructions. For determination of IL-17 promoter activity 15,000 293T cells were seeded in each well of a 96 well plate and transfected 24 hours later with a plasmid containing the IL-17 promoter controlling expression of firefly luciferase. Twenty-four hours post transfection, cells were treated with benzodiazepines and SAHA. Twenty-four hours post treatment, cell lysates were prepared using GLOLYSIS® buffer (PROMEGA®) and luciferase activity was determined using BRIGHTGLO® Luciferase Reagent (PROMEGA®) and read on a spectrophotometer following manufacturer's instructions.

RNA Expression Protocols

To evaluate the ability of Alprazolam to reactivate latent cells from patients we obtained PBMCs from two HIV-1 patients who had been suppressed on therapy for greater than 6 months. 10×106 PBMCs were divided between three conditions: DMSO control, 50 µM Ro5-3335 and 10 µm Alprazolam. PBMCs were cultured in RPMI with 10% FBS and the given drugs for twenty-four hours. RNA was extracted from the cells and used for RTqPCR to detect HIV-1 Gag mRNA. RNA was extracted using Trizol reagent (Invitrogen) following manufacturer's protocol. Following reverse transcription, the samples were diluted 1:50, and 2.5 microliters were used for quantitative PCR in a BioRad CFX384 qPCR machine. All mRNA analyses were normalized to GAPDH. Nucleic acid amplification was tracked by SYBR Green method. Primer pairs used for detection are shown in Table 1.

TABLE 1

| Gene | Primer 1 | Primer 2 |
|---|---|---|
| T-bet | SEQ ID NO: 1 GGTTGGAGGACACCGACTAA | SEQ ID NO: 2 ATCCTTCTTGAGCCCCACTT |
| IL-2 | SEQ ID NO: 3 AAACTCACCAGGATGCTCAC | SEQ ID NO: 4 GTCCCTGGGTCTTAAGTGAAAG |
| APOBEC3G | SEQ ID NO: 5 CCGAGGACCCGAAGGTTAC | SEQ ID NO: 6 TCCAACAGTGCTGAAATTCG |
| APOBEC3C | SEQ ID NO: 7 AGCGCTTCAGAAAAGAGTGG | SEQ ID NO: 8 AAGTTTCGTTCCGATCGTTG |
| RUNX1 | SEQ ID NO: 9 TGGTTTTCGCTCCGAAGGT | SEQ ID NO: 10 CATGAAGCACTGTGGGTACGA |
| STAH | SEQ ID NO: 11 GGTTTCCATGATTGGAGCTGA | SEQ ID NO: 12 GGGCCATACCCATAACCGAAT |
| IL-7R | SEQ ID NO: 13 CCCTCGTGGAGGTAAAGTGC | SEQ ID NO: 14 CCTTCCCGATAGACGACACTC |
| GAPDH | SEQ ID NO: 15 GCTCACTGGCATGGCCTTCCG TGT | SEQ ID NO: 16 TGGAGGAGTGGGTGTCGCTGT TGA |

Example 1: Reactivation of Latent HIV-1 by Benzodiazepines

Clinically prescribed benzodiazepine drugs (Table 2) was screened for reactivation of HIV-1, both alone and in conjunction with SAHA.

TABLE 2

Benzodiazepines tested for latent HIV-1 reactivation

| Benzodiazepine | Clinical use | Trade Name(s) |
|---|---|---|
| Alprazolam | Anxiolytic | Xanax |
| Bromazepam | Anxiolytic | Lecotopam, Lexotan, Lexillium, Lexaurin, Brazepam, Rekotnil, Bromaze, Somaliumand, Lexotanil |
| Clobazam | Anxiolytic, anticonvulsant | Frisium, Urbanol, Onfi, Tapclob |
| Clonazepam | Anxiolytic, anticonvulsant | Klonopin |
| Clorazepate | Anxiolytic | Tranxene, Novo-Clopate |
| Diazepam | Anxiolytic | Vallium |
| Estazolam | Hypnotic | Prosom, Eurodin |
| Flunitrazepam | Hypnotic | Rohypnol |

Figure 1B:
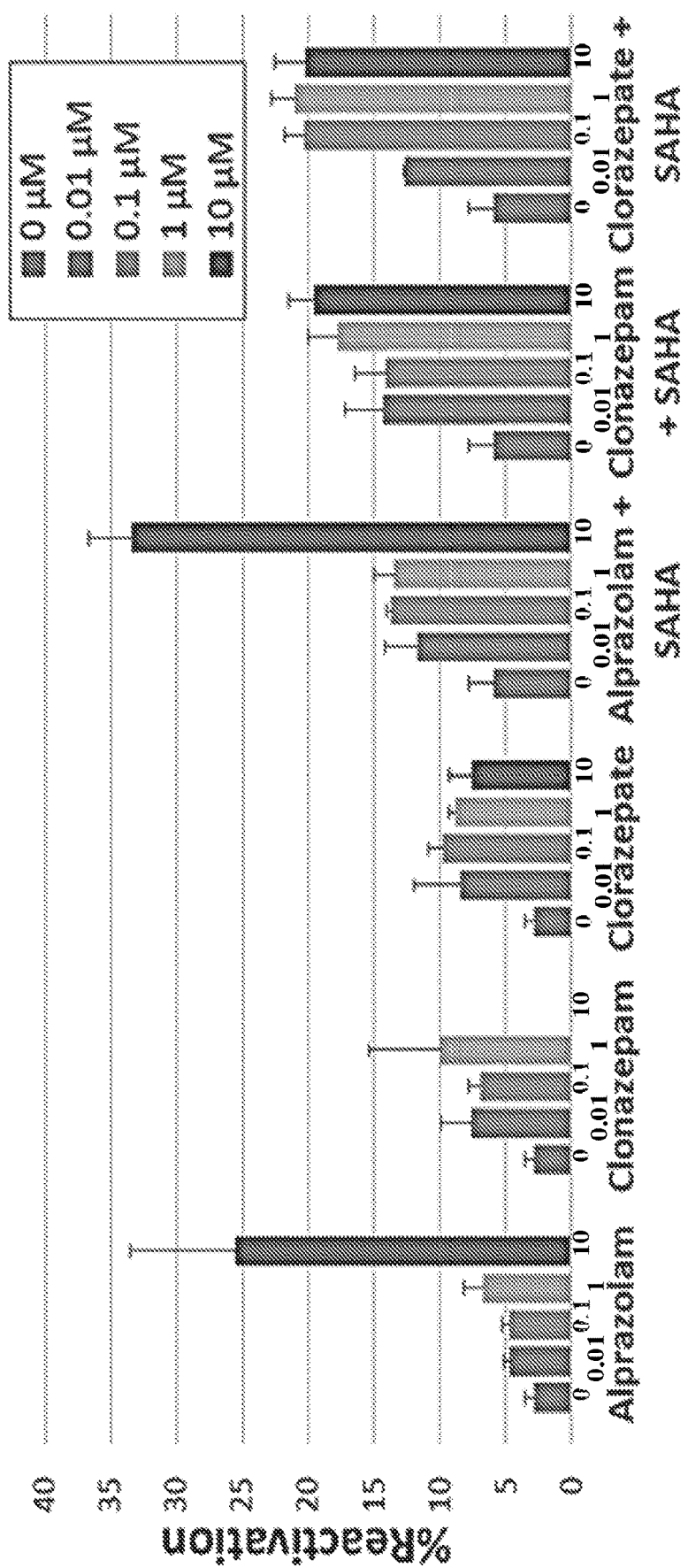

Reactivation of latent HIV-1 was tested using the JLat10.6 cell line model of T-cell latency (FIGS. 1A-1B). Reactivation was measured by flow cytometry as the percentage of GFP+ live cells following treatment with 10 µM benzodiazepine. Treatment with DMSO showed only a background level of GFP+ cells (2.8%). Ro5-3335 did not activate the virus by itself. When used independently, only Alprazolam, Diazepam, and Flunitrazepam showed significant activation compared to control (20.3%, 12.4% and 9.1% respectively). As expected, SAHA induced a modest increase in GFP+ cells (6.2%). When SAHA was used in combination with benzodiazepines all of the tested benzodiazepines showed a significant increase in GFP+ cells compared to SAHA alone (ranging from 10.2% to 22% GFP positive), Alprazolam and Diazepam showed maximum activation in the presence or absence of SAHA. Dose dependent reactivation was tested for Alprazolam, Clonazepam and Clorazepate (FIG. 1B) in the absence or presence of 0.5 uM SAHA. Alprazolam alone showed strong HIV-1 reactivation at 10 µM (25.5% compared to 2.8% for the DMSO control). Clonazepam and Clorazepate showed a smaller maximal effect, but at lower doses. When used in combination with SAHA, all three BZs showed an increase over SAHA alone. Alprazolam caused an increase in GFP+ cells ranging from 11.7% to 33.4% depending on dose as compared to 5.9% for SAHA alone. Clonazepam and Clorazepate also showed an increase in activation over SAHA alone, but to a lesser degree (maximum activation of 19.6% and 21.0% respectively).

Figure 2A:
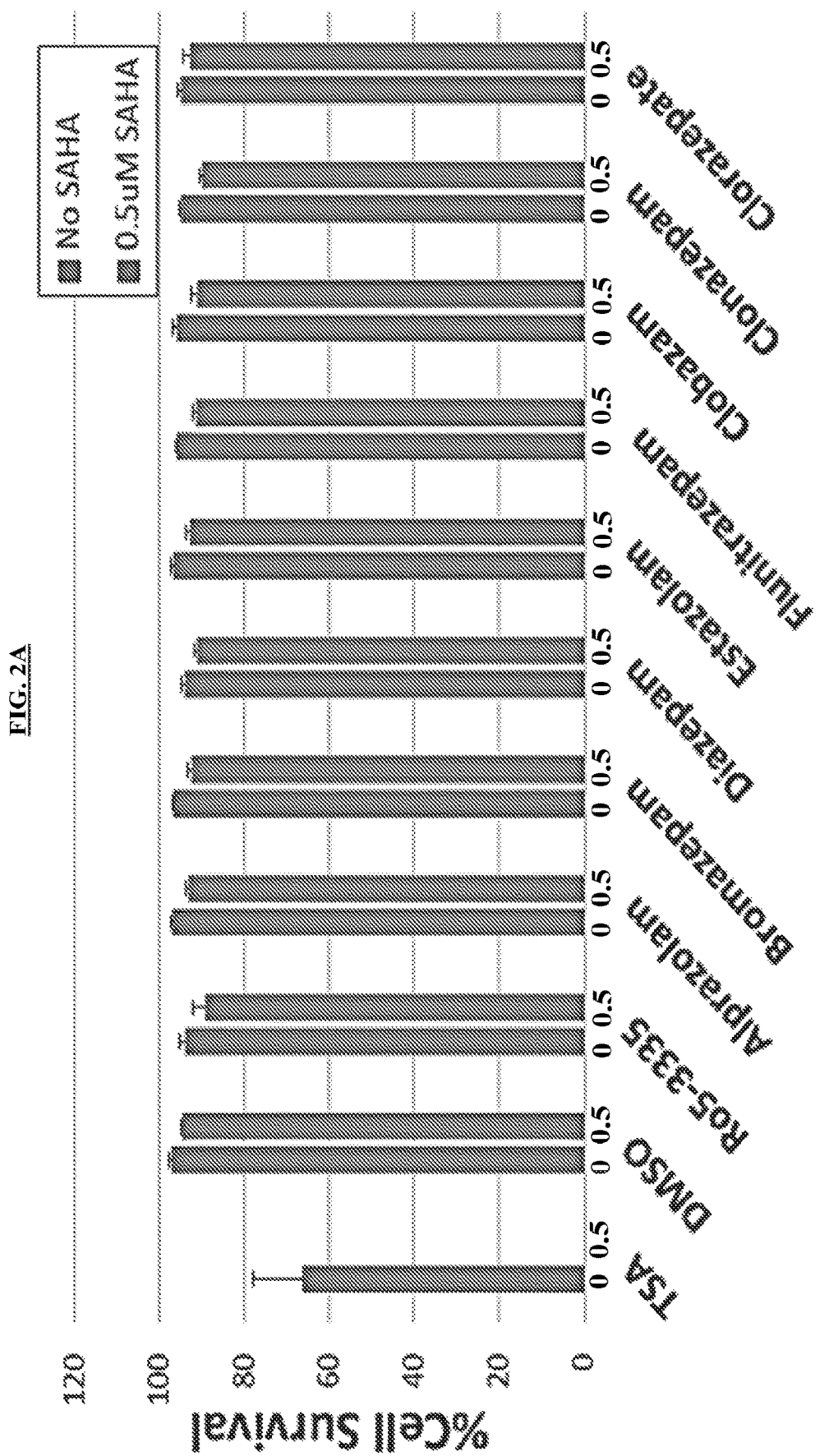
FIG. 2A is a graph reporting survival rate of JLat10.6 cells after exposure to benzodiazepine drugs after 48 hours of incubation. Trichostatin A (TSA) was used as a positive control for induced toxicity.

Example 2: Cellular Viability and Global T-Cell Activation in the Presence of Benzodiazepines To examine safety of the treatment and effect on T-cell activation, Jlat10.6 cells were treated with different benzodiazepines with and without SAHA. Forty-eight hours after incubation, cells were harvested and stained with red live/dead staining according to the manufacturer protocol (LIVE/DEAD® Fixable Red Dead Cell Stain Kit, ThermoFisher Scientific) (FIG. 2A). Trichostatin A, used as a positive control induced toxicity (68% viable). 0.5 µM SAHA caused a slight reduction in viability as compared to DMSO control (97% to 94.6%). No significant loss of viability was observed with benzodiazepine treatments.

Figure 2B:
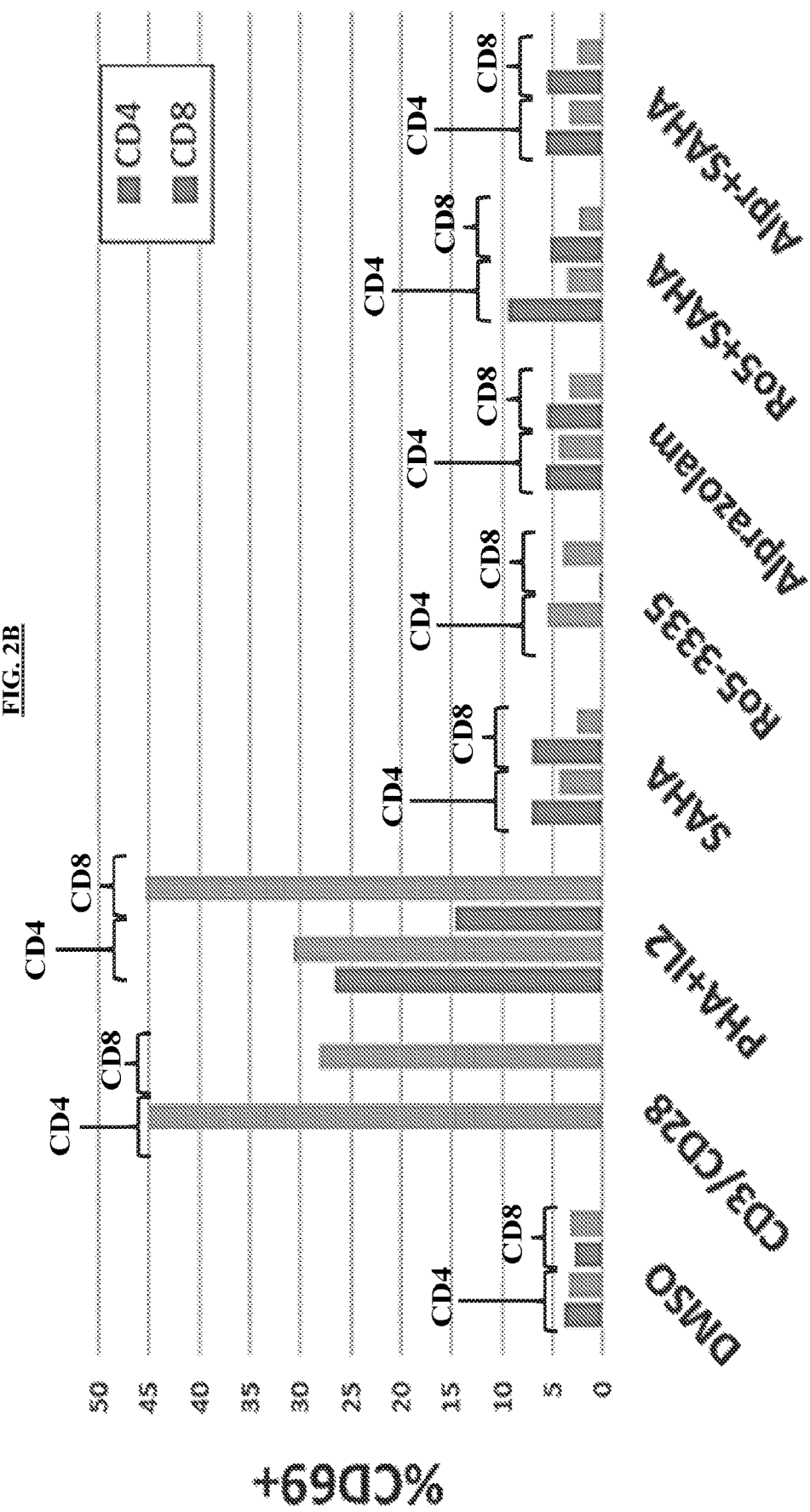
FIG. 2B is a graph reporting T-cell activation in a population of primary peripheral blood mononuclear cells (PBMCs) from health donors after exposure to alprazolam or Ro5-3335, each alone or in combination with SAHA. Treatment with alprazolam in combination with SAHA did not induce significant T-cell activation.

In order to investigate whether alprazolam was specifically activating HIV-1 or having a general effect on T cell activation (CD4 and CD8), primary peripheral blood mononuclear cells (PBMCs) from two healthy donors were treated with 10 µM Alprazolam or 50 µM Ro5-3335, both alone or in combination with 0.5 µM SAHA. Twenty-four hours after treatment, cells were stained using Zombie yellow live and dead staining, then stained for CD3, CD8, CD4, CD69, and then fixed for analysis by flow cytometry. AntiCD3/CD28 and PHA were included as a positive control (FIG. 2B). Treatment of Alprazolam in combination with SAHA did not induce any significant T cell activation.

Example 3: Epigenetic Effects of Alprazolam

SAHA increases the transcription of RUNX1. Without intending to be limited to any particular theory, this potential increase in RUNX1 expression can explain the observed synergy between SAHA and Ro5-3335. Using the NUCLEO-M imaging technique, which allows fluorescent imaging of intact, unfixed nuclei, this theory was explored at the protein level (FIG. 3A). Treatment of cells with SAHA led to an increase in acetylated H3K9 in the nuclei. Treatment with Ro5-3335 and SAHA further increased the acetylation in keeping with the observed synergy. Treatment with SAHA alone also increased the total presence of RUNX1 in the nuclei as expected. Inhibition of RUNX1 function by Ro5-3335 led to a decrease in RUNX1 detection. This is potentially due to the presence of RUNX binding sites in the RUNX1 promoter that respond positively to RUNX1 binding. Inhibition of RUNX1 by Ro5-3335 can block this activation and lead to the observed decrease in RUNX1 expression.

Figure 3B:
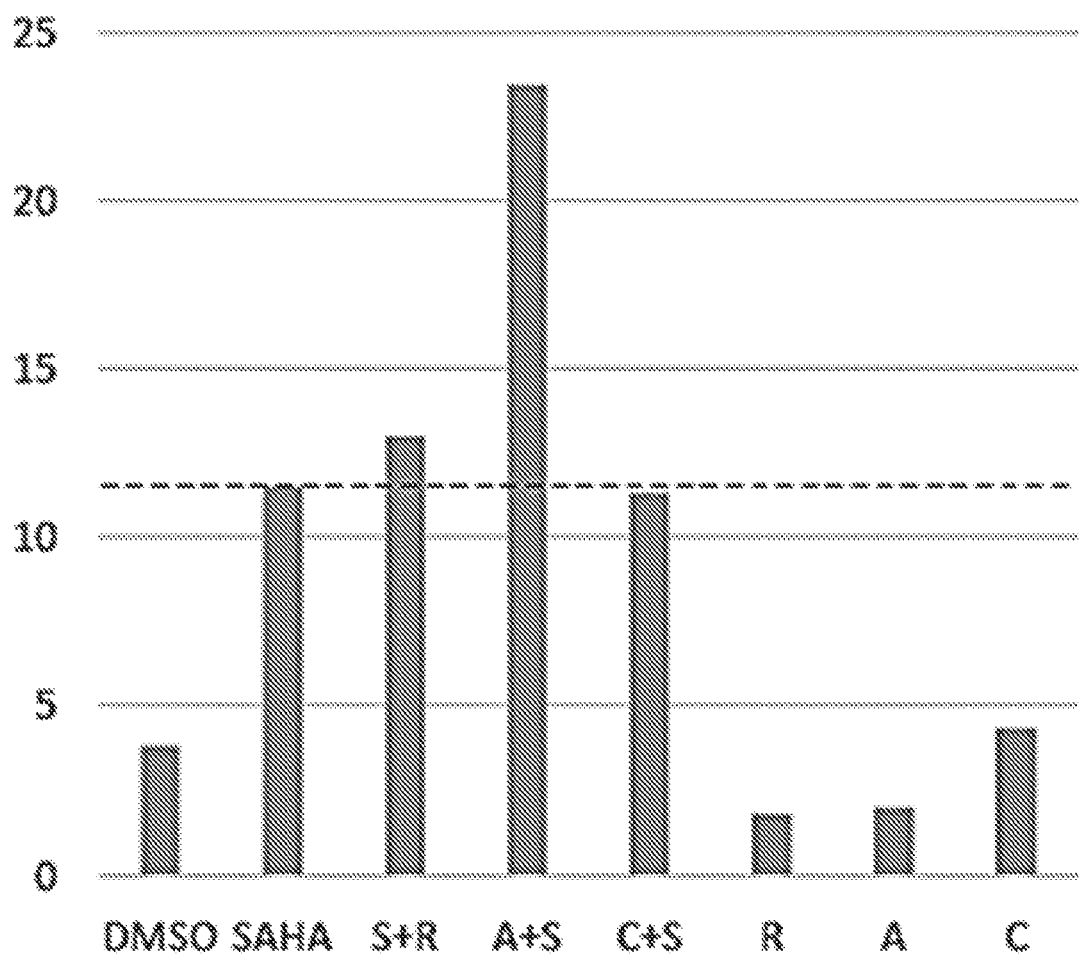

Without intending to be limited to any particular theory, the ability of Alprazolam to efficiently reactivate HIV-1 without SAHA suggests that it can operate through a different mechanism of action than Ro5-3335 and the other clinical benzodiazepines tested. In order to test the changes driven by these compounds, chromatin immunoprecipitation (ChIP) assays were performed to examine the presence of various proteins and modifications at the integrated HIV-1 long terminal repeat (LTR). TZMbl cells were treated for 48 hours with 50 µM Ro5-3335, 10 µM Alprazolam and 10 µM Clonazepam with or without 5 µM SAHA Acetylation of histone 3 at lysine 9 (H3K9ac) was first examined (FIG. 3B). Treatment of the cells with SAHA increased the occupancy of H3K9ac at the promoter as compared to DMSO control. Treatment of cells with Alprazolam further increased acetylation over SAHA alone. This potentiation was not seen with Ro5-3335 or Clonazepam. None of the benzodiazepines were able to alter H3K9ac when used alone.

Figure 3C:
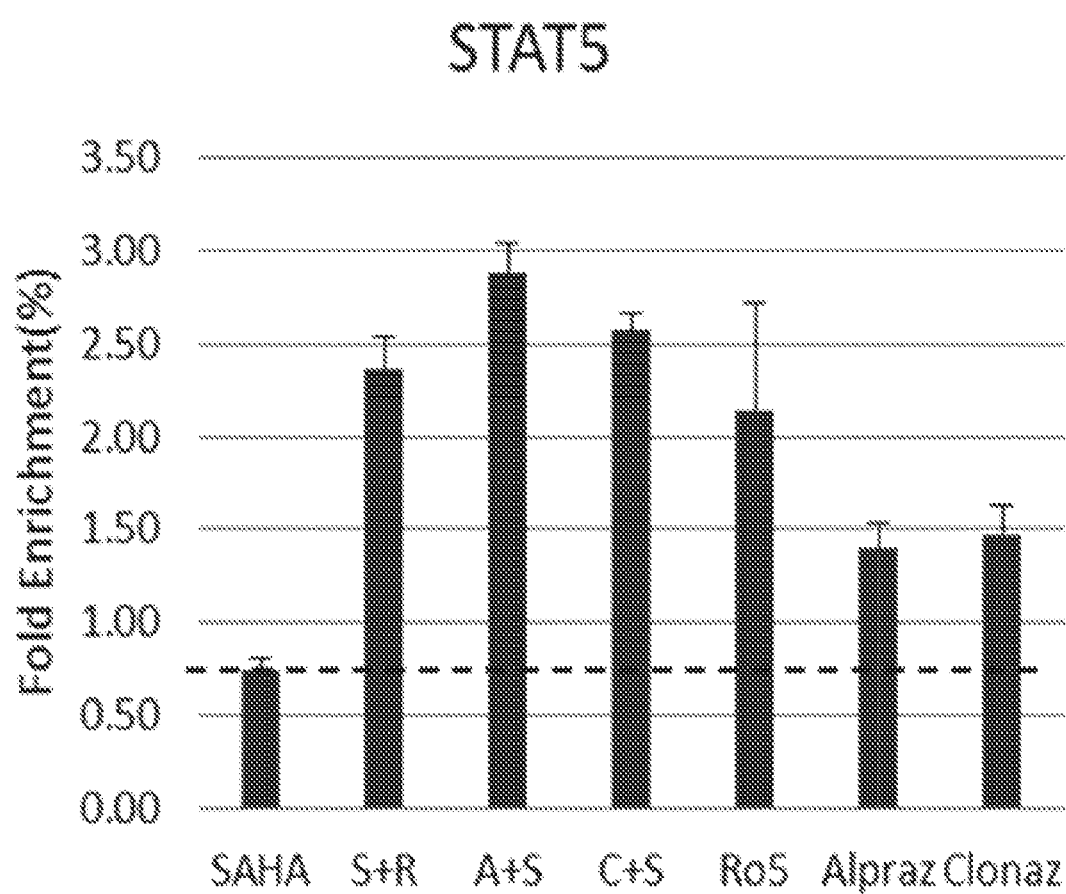

RUNX1 suppresses the function of the transcription factor STAT5 that has been shown to have a positive effect on HIV-1 transcription. Therefore, ChIP was performed for STAT5 to determine if benzodiazepine treatment might increase the recruitment of STAT5 above SAHA treatment (FIG. 3C). All three benzodiazepines were capable of driving recruitment of STAT5 to the promoter, and further recruitment was seen when used in combination with SAHA. STAT5 is capable of recruiting the histone acetyl transferase CBP/P300 that acetylates histone 3 at lysine 27, a residue that is not affected by SAHA. Additionally, this histone acetyl transferase has been shown to have activity in acetylating HIV-1 Tat protein and modulating its activity. ChIP for CBP/P300 showed no increase in recruitment upon treatment with SAHA alone (FIG. 3D). Addition of both Ro5-3335 and Alprazolam induced recruitment of CBP/P300 to the HIV-1 LTR (by 3 and 7 fold respectively).

Figure 3E:
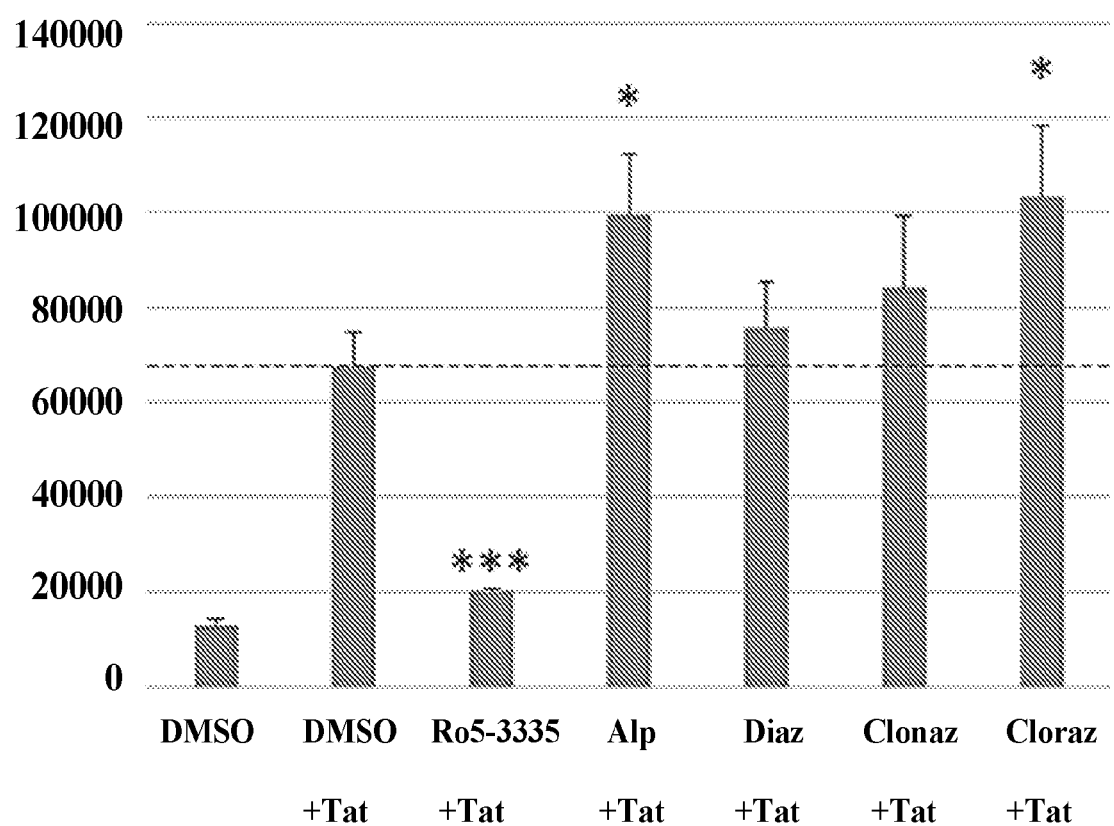
FIG. 3E is a graph showing Tat protein suppression in transfected TZMb1 cells after exposure to benzodiazepines as determined by luciferase assay. Only Ro5-3335 demonstrated significant suppression of Tat.

Ro5-3335 is an inhibitor of HIV-1 Tat transcriptional activity due to its RUNX suppressive activity, and interacts with the HIV-1 Tat protein. Tests were run to see if Ro5-3335 would suppress Tat transactivation when used in conjunction with SAHA and whether the other tested benzodiazepines might have the same effect. For these studies TZMbl cells were transfected in 96-well format with a plasmid encoding HIV-1 Tat, treated 24 hours later with benzodiazepines, and then reactivation was determined by luciferase assay 24 hours after treatment (FIG. 3E). Ro5-3335 significantly suppressed luciferase expression, consistent with its description as a Tat inhibitor. None of the benzodiazepines tested exhibited this suppression: Alprazolam and Clorazepate showed additional activation beyond what was seen with Tat alone. Without intending to be limited to any particular theory, this lack of Tat inhibition can explain why these drugs show better synergy or, in the case of Alprazolam and Diazepam, can activate latent virus without SAHA.

Example 4: Alprazolam Effect on RUNX1 Responsive Genes

It was then determined whether Alprazolam was a bona fide inhibitor of RUNX1 function. RUNX1 is known to form a complex with RORγt and bind to IL-17 enhancer and promoter to up-regulate IL-17 expression (Wong, et al., 2011, Immunology, 132(2):157-164; Zhang, et al., 2008, Nat Immunol 9(11):1297-1306).

Figure 4A:
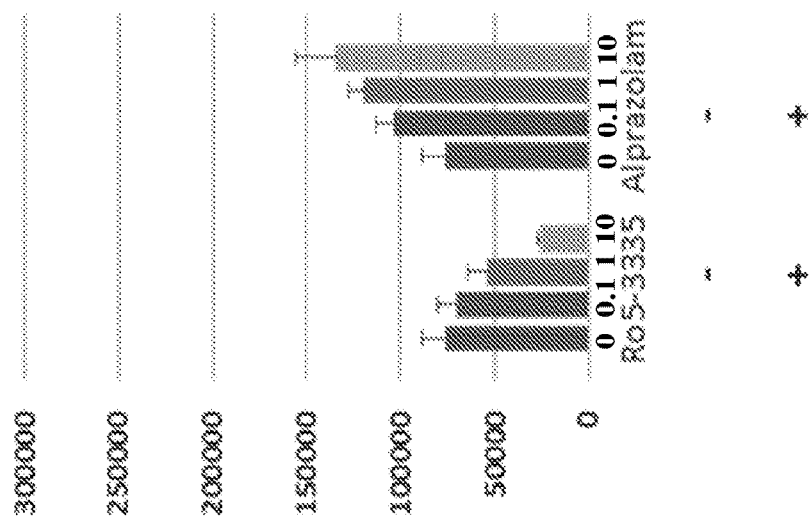
FIGS. 4A-4C are graphs showing the effects of Ro5-3335 and Alprazolam on RUNX1 function. The ability of Ro5-3335 and Alprazolam to alter expression of luciferase in 293T cells transfected with IL-17-luciferase reporter responsive promoter, each compound alone (FIG. 4A), in combination with SAHA (FIG. 4B), or in cells having an overexpression of RUNX1 (FIG. 4C).
Figure 4B:
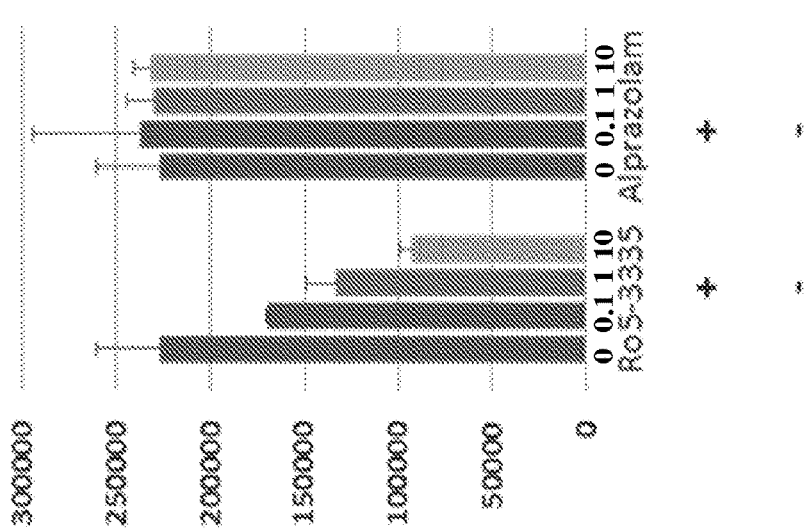
Figure 4C:
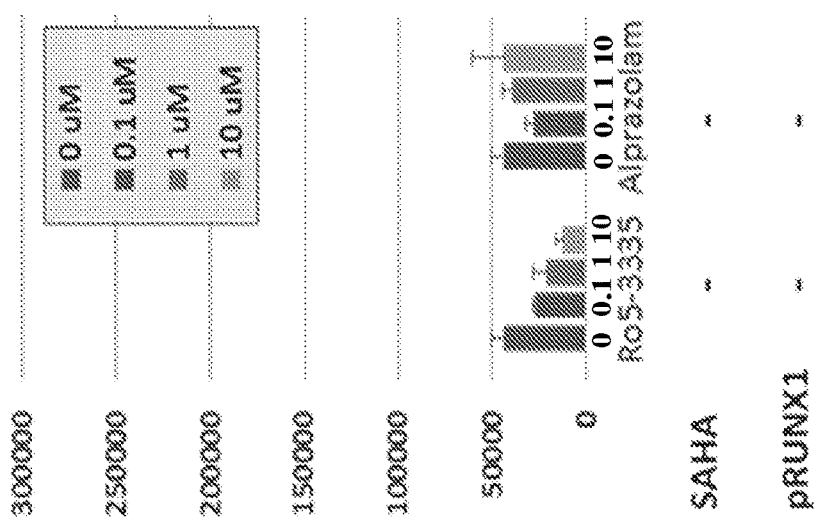

The ability of Ro5-3335 and Alprazolam to alter expression of luciferase under the control of the IL17 promoter was tested. It was hypothesized that a RUNX inhibitor would suppress activity of the IL17 promoter. 293T cells were transfected with IL-17-luciferase reporter responsive promoter and treated with Ro5-3335 and Alprazolam (FIG. 4A), with or without addition of SAHA (FIG. 4B) or overexpression of RUNX1 (FIG. 4C). Ro5-3335 inhibited IL-17 promoter in a dose dependent fashion in all three conditions. In the absence of SAHA or RUNX1 over expression, Alprazolam displayed a statistically significant suppression of IL-17 promoter activity at the lowest dose (0.1 µM), but not at higher doses. Treatment with SAHA or over expression of RUNX1 both increased IL-17 driven luciferase expression compared to control (FIGS. 4B-4C as compared to FIG. 4A). Alprazolam had no effect on luciferase activity in the presence of SAHA and increased luciferase activity in the setting of RUNX1 over expression. These experiments suggest that Alprazolam has an effect on the IL-17 promoter.

Figure 5:
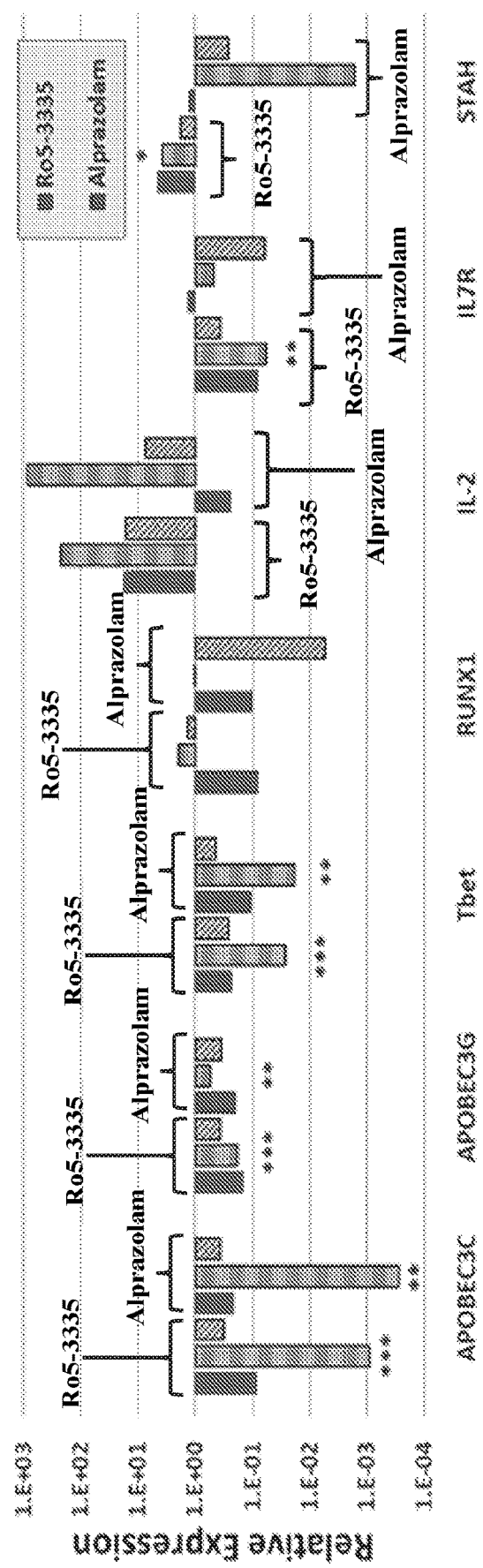
FIG. 5 is a graph showing the results of RUNX responsive gene expression assays after administration of Ro5-3335 and Alprazolam.

Next, expression of several RUNX responsive genes in PBMCs in response to Ro5-3335 and Alprazolam was examined. Samples from three HIV-1 patients were treated with Alprazolam or Ro5-3335 for 48 hours. RNA was harvested using Trizol and cDNA was synthesized using RT reaction. qPCR was performed using primers for seven known RUNX1 responsive genes: APOBEC3C, APOBEC3G, Tbet, RUNX1 d, IL-2, IL7R and STAH (FIG. 5). As a RUNX1 inhibitor, Ro5-3335 significantly altered the expression of five of the selected RUNX responsive genes. Similarly, Alprazolam treatment had a statistically significant effect on APOBEC3C, APOBEC3G and Tbet. Additionally, Alprazolam treatment altered RUNX1, IL-2 and IL7R expression in a manner similar to Ro5-3335, but without statistical significance.

Figure 6:
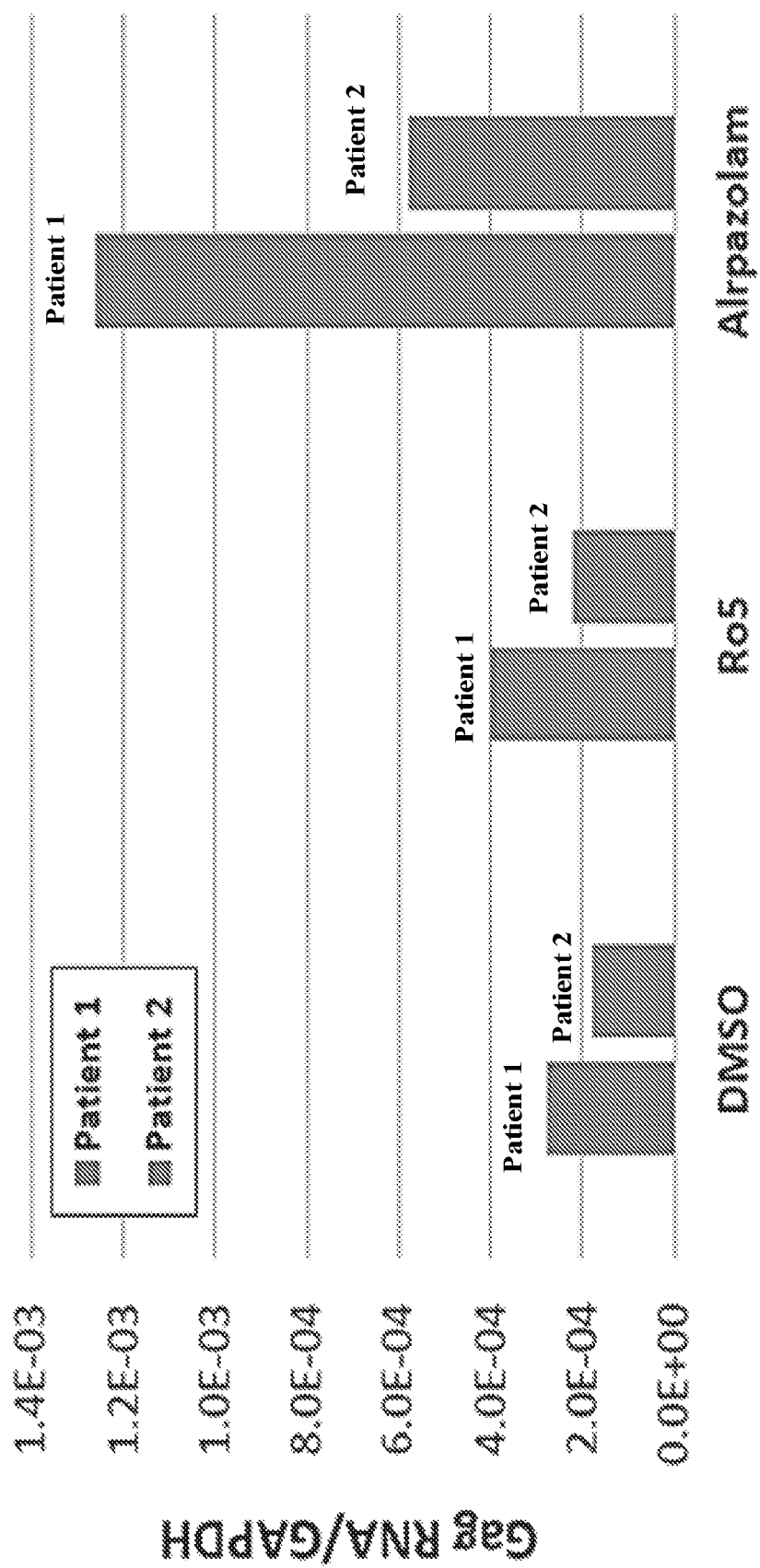
FIG. 6 is a graph showing HIV-1 Gag mRNA expression in latent cells from HIV-1 patients in the presence of Ro5-3335 and Alprazolam.

Example 5: Latency Reversal in Ex Vivo Stimulation of Patient PBMCs with Alprazolam In order to evaluate the ability of Alprazolam to reactivate latent cells from patients, PBMCs were obtained from two HIV-1 patients who had been suppressed on therapy for greater than 6 months. $10 \times 10^6$ PBMCs were divided between three conditions: DMSO control, 50 µM Ro5-3335 and 10 µm Alprazolam. PBMCs were cultured in RPMI with 10% FBS and the given drugs for twenty-four hours. RNA was extracted from the cells and used for RTqPCR to detected HIV-1 Gag mRNA (FIG. 6). The use of Ro5-3335 alone had a negligible effect on HIV-1 transcripts (1.5 and 1.2-fold increase). Treatment with Alprazolam produced detectable reactivation of HIV-1 transcripts. Patient 1 showed a 4.6-fold increase in HIV-1 Gag RNA, and Patient 2 showed a 3.3-fold increase.

The disclosures of each and every patent, patent application, and publication cited herein are hereby incorporated herein by reference in their entirety. While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A method of treating or ameliorating HIV infection in a subject infected with HIV, the method comprising administering to the subject a therapeutically effective amount of a benzodiazepine or a salt or solvate thereof, wherein the benzodiazepine is at least one selected from the group consisting of alprazolam, bromazepam, clobazam, clonazepam, clorazepate, diazepam, estazolam, and flunitrazepam.

2. A method of reactivating latent HIV-1 virus that has been integrated into the genome of a subject infected with HIV-1, the method comprising administering to the subject a therapeutically effective amount of a benzodiazepine or a salt or solvate thereof, wherein the benzodiazepine is at least one selected from the group consisting of alprazolam, bromazepam, clobazam, clonazepam, clorazepate, diazepam, estazolam, and flunitrazepam.

3. The method of claim 1, further comprising administering to the subject a therapeutically effective amount of a histone deacetylase inhibitor.

4. The method of claim 3, wherein the histone deacetylase inhibitor is selected from the group consisting of vorinostat (N-hydroxy-N'-phenyloctanediamide or suberoylanilide hydroxamic acid, SAHA), belinostat ((2E)-N-Hydroxy-3-3-(phenylsulfamoyl)phenyl]prop-2-enamide), LAQ824 ((E)-3-(4-((2-(1H-indol-3-yl)ethyl)(2-hydroxyethy)amino)methyl)phenyl)-N-hydroxyacrylamide), panobinostat ((2E)-N-hydroxy-3-[4-({[2-(2-methyl-1H-indol-3-yl)ethyl]amino}methyl)phenyl]acrylamide), givinostat ({6-[(diethylamino)methyl]naphthalen-2-yl}methyl [4-(hydroxycarbamoyl)phenyl]carbamate), pyroxamide (N1-Hydroxy-N8-3-pyridinyl-octanediamide), trichostatin A ([R-(E,E)]-7-[4-(Dimethylamino) phenyl]-N-hydroxy-4,6-dimethyl-7-oxo-2,4-heptadienamide), CBHA (m-carboxy cinnamic acid bis-hydroxamide), and any combinations thereof.

5. A method of reactivating latent HIV-1 virus in a subject infected with HIV-1, wherein the method comprises administering to the subject a therapeutically effective amount of a benzodiazepine or a salt or solvate thereof, wherein the benzodiazepine is at least one selected from the group consisting of alprazolam, bromazepam, clobazam, clonazepam, clorazepate, diazepam, estazolam, and flunitrazepam; and wherein the method further comprises administering to the subject a therapeutically effective amount of a histone deacetylase inhibitor.

6. The method of claim 1, further comprising administering to the subject at least one additional compound useful for ameliorating or treating HIV infection, wherein the compound is selected from the group consisting of antiretroviral drugs, nucleoside/nucleotide reverse transcriptase inhibitors (NRTIs), non-nucleoside reverse transcriptase inhibitors (NNRTIs), protease inhibitors (PIs), fusion inhibitors, C-C chemokine receptor type 5 (CCR5) antagonists, and integrase inhibitors.

7. The method of claim 1, wherein the benzodiazepine is at least one selected from the group consisting of bromazepam, clobazam, clonazepam, clorazepate, diazepam, estazolam, and flunitrazepam.

8. The method of claim 1, wherein the benzodiazepine is at least one selected from the group consisting of bromazepam, clobazam, clonazepam, clorazepate, diazepam, and flunitrazepam.

9. The method of claim 2, further comprising administering to the subject a therapeutically effective amount of a histone deacetylase inhibitor.

10. The method of claim 9, wherein the histone deacetylase inhibitor is selected from the group consisting of vorinostat (N-hydroxy-N'-phenyloctanediamide or suberoylanilide hydroxamic acid, SAHA), belinostat ((2E)-N-Hydroxy-3-[3-(phenylsulfamoyl)phenyl]prop-2-enamide), LAQ824 ((E)-3-(4((2-(1H-indol-3-yl)ethyl)(2-hydroxyethy)amino)methyl)phenyl)-N -hydroxyacrylamide), panobinostat ((2E)-N-hydroxy-3-4-({[2-(2-methyl-1H-indol-3-yl)ethyl]amino}methyl)phenyl]acrylamide), givinostat ({6-[(diethylamino)methyl]naphthalen-2-yl}methyl [4-(hydroxycarbamoyl)phenyl]carbamate), pyroxamide (N1-Hydroxy-N8-3-pyridinyl -octanediamide), trichostatin A ([R-(E,E)]-7-[4-(Dimethylamino) phenyl]-N-hydroxy-4,6-dimethyl-7-oxo-2,4-heptadienamide), CBHA (m-carboxy cinnamic acid bis-hydroxamide), and any combinations thereof.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: T-bet Primer 1

<400> SEQUENCE: 1
ggttggagga caccgactaa                                                   20

<210> SEQ ID NO 2
<211> LENGTH: 20
<212> TYPE: DNA
<213> ORGANISM: Artificial Sequence
<220> FEATURE:
<223> OTHER INFORMATION: T-bet Primer 2

<400> SEQUENCE: 2
atccttcttg agccccactt                                                   20

<210> SEQ ID NO 3
<211> LENGTH: 20
<212> TYPE: DNA
<213> ORGANISM: Artificial Sequence
<220> FEATURE:
<223> OTHER INFORMATION: IL-2 Primer 1

<400> SEQUENCE: 3
aaactcacca ggatgctcac                                                   20

<210> SEQ ID NO 4
<211> LENGTH: 22
<212> TYPE: DNA
<213> ORGANISM: Artificial Sequence
<220> FEATURE:
<223> OTHER INFORMATION: IL-2 Primer 2
```

-continued

```
<400> SEQUENCE: 4
gtccctgggt cttaagtgaa ag                                            22

<210> SEQ ID NO 5
<211> LENGTH: 19
<212> TYPE: DNA
<213> ORGANISM: Artificial Sequence
<220> FEATURE:
<223> OTHER INFORMATION: APOBEC3G Primer 1

<400> SEQUENCE: 5
ccgaggaccc gaaggttac                                                19

<210> SEQ ID NO 6
<211> LENGTH: 20
<212> TYPE: DNA
<213> ORGANISM: Artificial Sequence
<220> FEATURE:
<223> OTHER INFORMATION: APOBEC3G Primer 2

<400> SEQUENCE: 6
tccaacagtg ctgaaattcg                                               20

<210> SEQ ID NO 7
<211> LENGTH: 20
<212> TYPE: DNA
<213> ORGANISM: Artificial Sequence
<220> FEATURE:
<223> OTHER INFORMATION: APOBEC3C Primer 1

<400> SEQUENCE: 7
agcgcttcag aaaagagtgg                                               20

<210> SEQ ID NO 8
<211> LENGTH: 20
<212> TYPE: DNA
<213> ORGANISM: Artificial Sequence
<220> FEATURE:
<223> OTHER INFORMATION: APOBEC3C Primer 2

<400> SEQUENCE: 8
aagtttcgtt ccgatcgttg                                               20

<210> SEQ ID NO 9
<211> LENGTH: 19
<212> TYPE: DNA
<213> ORGANISM: Artificial Sequence
<220> FEATURE:
<223> OTHER INFORMATION: RUNX1 Primer 1

<400> SEQUENCE: 9
tggttttcgc tccgaaggt                                                19

<210> SEQ ID NO 10
<211> LENGTH: 21
<212> TYPE: DNA
<213> ORGANISM: Artificial Sequence
<220> FEATURE:
<223> OTHER INFORMATION: RUNX1 Primer 2

<400> SEQUENCE: 10
catgaagcac tgtgggtacg a                                             21

<210> SEQ ID NO 11
<211> LENGTH: 21
```

```
<212> TYPE: DNA
<213> ORGANISM: Artificial Sequence
<220> FEATURE:
<223> OTHER INFORMATION: STAH Primer 1

<400> SEQUENCE: 11
ggtttccatg attggagctg a                                              21

<210> SEQ ID NO 12
<211> LENGTH: 21
<212> TYPE: DNA
<213> ORGANISM: Artificial Sequence
<220> FEATURE:
<223> OTHER INFORMATION: STAH Primer 2

<400> SEQUENCE: 12
gggccatacc cataaccgaa t                                              21

<210> SEQ ID NO 13
<211> LENGTH: 20
<212> TYPE: DNA
<213> ORGANISM: Artificial Sequence
<220> FEATURE:
<223> OTHER INFORMATION: IL-7R Primer 1

<400> SEQUENCE: 13
ccctcgtgga ggtaaagtgc                                                20

<210> SEQ ID NO 14
<211> LENGTH: 21
<212> TYPE: DNA
<213> ORGANISM: Artificial Sequence
<220> FEATURE:
<223> OTHER INFORMATION: IL-7R Primer 2

<400> SEQUENCE: 14
ccttcccgat agacgacact c                                              21

<210> SEQ ID NO 15
<211> LENGTH: 24
<212> TYPE: DNA
<213> ORGANISM: Artificial Sequence
<220> FEATURE:
<223> OTHER INFORMATION: GAPDH Primer 1

<400> SEQUENCE: 15
gctcactggc atggccttcc gtgt                                           24

<210> SEQ ID NO 16
<211> LENGTH: 24
<212> TYPE: DNA
<213> ORGANISM: Artificial Sequence
<220> FEATURE:
<223> OTHER INFORMATION: GAPDH Primer 2

<400> SEQUENCE: 16
tggaggagtg ggtgtcgctg ttga                                           24
```